(12) United States Patent
Bruce et al.

(10) Patent No.: US 12,420,234 B2
(45) Date of Patent: Sep. 23, 2025

(54) FILTER ASSEMBLY, KIT AND METHODS

(71) Applicant: Nature Metrics Ltd, Surrey (GB)

(72) Inventors: Catherine Bruce, Surrey (GB); Cuong Tang, Surrey (GB); Scott Townend, Surrey (GB)

(73) Assignee: Nature Metrics Ltd., Surrey (GB)

( * ) Notice: Subject to any disclaimer, the term of this patent is extended or adjusted under 35 U.S.C. 154(b) by 1089 days.

(21) Appl. No.: 17/416,097

(22) PCT Filed: Dec. 20, 2019

(86) PCT No.: PCT/GB2019/053649
§ 371 (c)(1),
(2) Date: Jun. 18, 2021

(87) PCT Pub. No.: WO2020/128503
PCT Pub. Date: Jun. 25, 2020

(65) Prior Publication Data
US 2022/0081686 A1 Mar. 17, 2022

(30) Foreign Application Priority Data

Dec. 21, 2018 (GB) .................................... 1820992

(51) Int. Cl.
*B01D 61/14* (2006.01)
*B01D 37/02* (2006.01)
(Continued)

(52) U.S. Cl.
CPC ........... *B01D 61/14* (2013.01); *B01D 37/025* (2013.01); *B01D 63/08* (2013.01); *B01D 69/02* (2013.01);
(Continued)

(58) Field of Classification Search
CPC .. C12N 1/06; C12N 15/1003; C12N 15/1017; B01D 37/025; B01D 61/14; B01D 63/08;
(Continued)

(56) References Cited

U.S. PATENT DOCUMENTS 5,139,031 A * 8/1992 Guirguis ................ A61B 5/153
600/584
9,265,883 B2 2/2016 Kim
(Continued)

FOREIGN PATENT DOCUMENTS

DE 102018113619 A1 12/2019
EP 1873231 A1 1/2008
WO WO-2017143452 A1 8/2017

OTHER PUBLICATIONS

International Search Report and Written Opinion of the International Application No. PCT/GB2019/053649, mailed Apr. 17, 2020.

*Primary Examiner* — John Kim
(74) *Attorney, Agent, or Firm* — MARSHALL, GERSTEIN & BORUN LLP

(57) ABSTRACT

The present invention is directed to a filter assembly for capturing environmental DNA (eDNA), a kit comprising the filter assembly, a method of capturing eDNA using the filter assembly, a method of analysing eDNA captured in the filter assembly, and a method of providing biodiversity data by analysing eDNA collected in the filter assembly.

8 Claims, 2 Drawing Sheets

(51) Int. Cl.
  *B01D 63/08*   (2006.01)
  *B01D 69/02*   (2006.01)
  *C12N 1/06*    (2006.01)
  *C12N 15/10*   (2006.01)
  *G01N 1/10*    (2006.01)
  *G01N 1/40*    (2006.01)
  *G16B 10/00*   (2019.01)

(52) U.S. Cl.
  CPC ........... *C12N 1/06* (2013.01); *C12N 15/1003* (2013.01); *C12N 15/1017* (2013.01); *G01N 1/10* (2013.01); *G01N 1/4005* (2013.01); *G01N 1/4077* (2013.01); *G16B 10/00* (2019.02); *B01D 2313/04* (2013.01); *B01D 2313/20* (2013.01); *B01D 2313/243* (2013.01); *B01D 2319/025* (2013.01); *B01D 2319/06* (2013.01); *B01D 2325/0283* (2022.08); *G01N 2001/1025* (2013.01); *G01N 2001/4088* (2013.01)

(58) Field of Classification Search
  CPC ................ B01D 69/02; B01D 2313/04; B01D 2313/20; B01D 2313/243; B01D 2319/025; B01D 2319/06; B01D 2325/0283; G16B 10/00; G01N 1/10; G01N 1/4005; G01N 1/4077; G01N 2001/1025; G01N 2001/4088
  See application file for complete search history.

(56) References Cited

U.S. PATENT DOCUMENTS

| | | | |
|---|---|---|---|
| 2010/0187230 A1* | 7/2010 | Beer | B65D 77/225 29/428 |
| 2011/0233148 A1 | 9/2011 | Antonchuk et al. | |
| 2013/0264266 A1* | 10/2013 | Shick | B01D 63/087 210/417 |
| 2014/0308166 A1* | 10/2014 | Fletcher | A61B 5/150755 422/68.1 |
| 2016/0025607 A1* | 1/2016 | Sitton | G01N 1/4077 435/287.1 |
| 2016/0367745 A1* | 12/2016 | Liu | A61M 1/1672 |

* cited by examiner

FILTER ASSEMBLY, KIT AND METHODS

CROSS-REFERENCE TO RELATED APPLICATION

This present application is the US national phase of International Patent Application No. PCT/GB2019/053649, filed Dec. 20, 2019, which claims priority to United Kingdom Application No. 1820992.4, filed Dec. 21, 2018. The priority application, GB 1820992.4, is hereby incorporated by reference in its entirety.

FIELD OF THE INVENTION

The present invention is directed to a filter assembly for capturing environmental DNA (eDNA), a kit comprising the filter assembly, a method of capturing eDNA using the filter assembly, a method of analysing eDNA captured in the filter assembly, and a method of providing biodiversity data by analysing eDNA collected in the filter assembly.

BACKGROUND TO THE INVENTION

Environmental DNA or eDNA is DNA that is collected from a variety of environmental samples such as soil, water, or even air rather than directly sampled from an individual organism. As various organisms interact with the environment, DNA is expelled and accumulates in their surroundings. Example sources of eDNA include, but are not limited to, faeces, mucus, gametes, shed skin, carcasses and hair. Such samples can be analysed by a variety of molecular methods to detect the presence of particular species or to generate species lists.

Aquatic eDNA can be captured by passing a sample of water through a filter membrane. Cellular and extra-cellular material containing DNA is trapped on the filter membrane and can be used to identify the species present in the waterbody. Challenges facing current approaches to eDNA capture include the risk of contamination from the sampler or the environment and the tendency of the membrane to become clogged with suspended particulate matter in the sample. Early clogging of the membrane reduces the volume of sample which can be filtered. A small sample volume may not be sufficient for an eDNA survey.

SUMMARY OF THE INVENTION

In a first aspect, the present invention provides a filter assembly comprising: a first membrane; a second membrane; a fluid-impermeable housing; an inlet; and an outlet.

In a second aspect, the present invention provides a kit comprising a filter assembly according to the first aspect and one or more syringe, wherein the one or more syringe is configured to be fixed to the inlet of the filter assembly.

In a third aspect, the present invention provides a method of capturing environmental DNA (eDNA) comprising: introducing a sample containing eDNA into an inlet of a filter assembly according to the first aspect; passing the sample through the first membrane and the second membrane of the filter assembly; and passing the sample out of the filter assembly though the outlet.

In a fourth aspect, the present invention provides a method of providing eDNA comprising: providing a filter assembly comprising captured eDNA; and extracting eDNA from the filter assembly.

In a fifth aspect, the present invention provides a method of providing biodiversity data by analysing eDNA collected in a filter assembly according to the first aspect of the invention, or collected using a kit according to the second aspect of the invention, or collected by a method according to the third aspect of the invention.

DETAILED DESCRIPTION OF THE INVENTION

Figure 1:
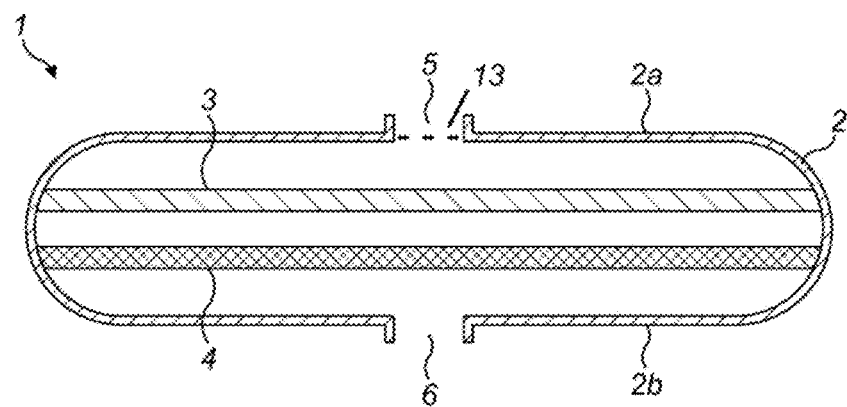
FIG. 1 is a cross section view of a filter assembly according to an embodiment of the first aspect of the present invention.

In a first aspect, the present invention provides a filter assembly comprising: a first membrane; a second membrane; a fluid-impermeable housing; an inlet; and an outlet. The inlet is typically disposed on a first face of the fluid-impermeable housing, and the outlet is typically disposed on a second face of the fluid-impermeable housing. The first membrane may be disposed within the fluid-impermeable housing between the first face of the fluid-impermeable housing and the second face of the fluid-impermeable housing. The second membrane may be disposed within the fluid-impermeable housing between the first membrane and the second face of the fluid-impermeable housing. The first membrane and/or the second membrane are typically fluid permeable membranes.

Preferably, the filter assembly is for isolating eDNA from a sample, such as an environmental sample. In a particularly preferred embodiment, the sample is a liquid sample, such as a sample from a body of water. The purpose of the filter assembly is to separate the eDNA and material containing eDNA from the rest of the sample, such as the water or other fluid.

It has been found that a filter assembly according to the first aspect of the invention can increase the volume of eDNA-containing sample which can be filtered, can reduce the time required for filtration and can reduce the risk of sample contamination.

Providing a first membrane allows pre-filtering of the sample and may remove particulate matter from the sample before the sample is passed through a second membrane which may retain eDNA-containing material. Locating the first and second membranes in a fluid-impermeable housing avoids the increased contamination risk, and added time delay which would otherwise be associated with having a separate pre-filtering step prior to filtration. Locating the first and second membranes in a fluid-impermeable housing also reduces cost since eDNA can be extracted from both the filter and the pre-filter in a single extraction step.

The inlet and the outlet are typically the only means of fluid communication between the interior of the filter assembly and the exterior of the filter assembly.

The pore size of the first membrane is typically referred to herein as the "first pore size". The pore size of the second membrane is typically referred to herein as the "second pore size". The first pore size is typically greater than the second pore size. The first pore size is typically about 1 µm or more, and the second pore size is suitable for capturing eDNA in the retentate of the second membrane, and is typically about 1 μm or less.

As used herein, the pore size of a membrane typically refers to the mean maximum dimension of the membrane's pores as measured by scanning electron microscopy (SEM).

As used herein, the term "about" typically refers to a permitted degree of deviation from a stated value which would be considered reasonable to a skilled person. The term "about" as used herein may refer to a permitted degree of deviation from a stated value of ±10% of that value.

In some embodiments, particularly when the filter assembly is intended for use in filtering a sample from a water body such as a pond, lake, stream or river, the first pore size is from about 2 μm to about 10 μm, e.g. from about 3 μm to about 7 μm, or from about 4 μm to about 6 μm. In such embodiments, the first pore size may be about 5 μm (e.g. 5±0.5 μm). However, in other embodiments, it may be preferable to have a larger first pore size (e.g. about 10 μm or more). Larger first pore sizes may be preferable in embodiments when the filter assembly is intended for use in heavily sedimented or turbid water.

The second pore size is preferably from about 0.5 μm to about to 1.0 μm, more preferably from about 0.6 μm to about 1.0 μm, still more preferably from about 0.7 μm to about 0.9 μm. Particularly preferably, the second pore size is about 0.8 μm (e.g. 0.8±0.08 μm).

The first membrane is typically formed of a hydrophilic material. The first membrane is preferably a glass fibre membrane.

The second membrane is typically formed of a hydrophilic material. The second filter is preferably a polyethersulfone or cellulose membrane.

The filter assembly is configured so that a sample is introduced into the filter assembly via the inlet. The sample then passes through the first membrane, creating a first retentate and a first filtrate. The first filtrate then passes through the second membrane, creating a second retentate and a second filtrate. The second filtrate then leaves the filter assembly via the outlet, whilst both the first and second retentates remain within the housing of the filter assembly.

In some embodiments, the inlet and outlet are sealed to prevent contamination of the filter assembly before or after use. In particular, the inlet and outlet do not allow fluid to enter or exit the fluid assembly.

In some embodiments, the inlet and/or outlet comprises a valve configured to allow fluid to pass through under pressure, but is sealed in the absence of pressure.

The inlet may be configured to form a fluid-impermeable seal with an outlet of a syringe and/or a pump. The fluid-impermeable seal is typically a releasable fluid-impermeable seal. For example, the inlet may have a Luer lock configuration.

The inlet may be configured to form a fluid-impermeable seal with a fluid-impermeable cap. The fluid-impermeable seal is typically a releasable fluid-impermeable seal. For example, the inlet may have a Luer lock configuration.

The outlet may be configured to form a fluid-impermeable seal with a fluid-impermeable cap and/or a pump. The fluid-impermeable seal is typically a releasable fluid-impermeable seal. For example, the outlet may have a Luer lock configuration.

In a second aspect, the present invention provides a kit comprising a filter assembly according to the first aspect and one or more syringe, wherein the one or more syringe is configured to be fixed to the inlet of the filter assembly. In the second aspect of the invention, the features of the filter assembly are as described elsewhere herein with reference to the first aspect of the invention.

The one or more syringe may be configured to form a fluid-impermeable seal with the inlet of the filter assembly. The fluid-impermeable seal is typically a releasable fluid-impermeable seal. The one or more syringe may have a Luer lock configuration.

In some embodiments of the kit, the inlet of the filter assembly and the one or more syringe may have complementary configurations suitable for forming a seal between the one or more syringe and the filter assembly (e.g. a releasable fluid-impermeable seal between the one or more syringe and the filter assembly). The inlet of the filter assembly and the one or more syringe preferably each have a Luer lock configuration.

The kit may be used to filter a sample, such as an environmental sample, for example, a sample from a body of water. In some embodiments, this involves filling a syringe with the sample and the syringe is then attached to the inlet of the filter assembly. The plunger of the syringe is then activated to force the sample through the inlet of the filter assembly and through the two membranes. The second filtrate is forced out of the filter assembly via the outlet. This may be repeated until all of the sample has been filtered.

In another embodiment, the sample may be fed through the filter assembly using a pump which may or may not form part of the kit. The pump may connect to the inlet and push the sample through the filter assembly, or the pump may connect to the outlet and draw the sample through the filter assembly.

Once all of the sample has been passed through the filter assembly, the inlet and outlet may be additionally sealed using caps.

At least one of the one or more syringes included in the kit may contain a preservative. This syringe may be pre-filled with a preservative which is to be injected into the filter assembly once the sample has been filtered. The preservative is described in more detail below with reference to the method of the third aspect.

The syringe may contain sufficient preservative to fill the filter assembly. For example, in some embodiments, the syringe may be a 1 ml, a 1.5 ml or a 2 ml syringe.

In use, syringe containing preservative may be attached to the inlet of the filter assembly after the sample has been filtered. The plunger of the syringe is then activated to force the preservative into the filter assembly.

The kit may comprise a plurality of syringes. In some embodiments, the kit comprises a syringe comprising a preservative, and further comprises a syringe suitable for introducing a sample into the inlet of the filter assembly.

In some embodiments, the syringe for introducing the sample is a large volume syringe, for example a 50 ml, 75 ml, 100 ml, or 150 ml syringe.

The kit may further comprise one or more fluid-impermeable cap (e.g. two or more fluid impermeable caps, typically two fluid-impermeable caps). The one or more fluid impermeable cap is typically configured to form a fluid-impermeable seal with the inlet and/or the outlet of the filter assembly. The fluid-impermeable seal is typically a releasable fluid-impermeable seal. The one or more cap may have a Luer lock configuration.

In some embodiments of the kit, the inlet and the outlet of the filter assembly, the one or more syringe, and the one or more fluid impermeable cap may have complementary configurations suitable for forming a seal between the one or more syringe and the inlet of the filter assembly (e.g. a releasable fluid-impermeable seal between the one or more syringe and the filter assembly), and suitable for forming a seal between the inlet and/or the outlet of the filter assembly and the one or more fluid-impermeable cap (e.g. a releasable fluid-impermeable seal between the inlet of the filter assembly and the one or more fluid impermeable cap). The inlet and the outlet of the filter assembly, the one or more syringe, and the one or more fluid impermeable cap preferably each have a Luer lock configuration.

In certain embodiments the kit may further comprise one or more of the following components:
  sampling vessel (e.g. sampling tube)
  means for attaching sampling vessel to a rod-like member (e.g. a cable tie)
  collection vessel (e.g. collection bag)
  packaging means (e.g. zip lock bag and/or envelope)
  gloves to be worn by the person using the filter assembly In some embodiments, the kit may also include instructions for using the kit, and/or an envelope suitable for mailing the filter assembly with captured eDNA to a laboratory for analysis.

In a third aspect, the present invention provides a method of capturing environmental DNA (eDNA) comprising: introducing a sample comprising eDNA into an inlet of a filter assembly according to the first aspect; passing the sample through the first membrane and the second membrane of the filter assembly; and passing the filtered sample out of the filter assembly though the outlet. In the method of the third aspect of the present invention at least a portion of the eDNA introduced into the filter assembly is typically retained within the filter assembly (e.g. on the first and/or second membrane) when the filtered sample is passed out of the filter assembly.

In some embodiments, the method of capturing environmental DNA (eDNA) comprises use of the kit according to the second aspect of the invention.

In some embodiments the sample may be introduced into the inlet of the filter assembly using a syringe. In other embodiments the sample may be introduced into the inlet of the filter assembly and passed through the filter assembly using a pump. In such other embodiments, a pump may be fixed to the inlet of the filter assembly (i.e. the pump may act to "push" the sample through the filter assembly), and/or may be fixed to the outlet of the filter assembly (i.e. the pump may act to "pull" the sample through the filter assembly).

In embodiments in which the sample is introduced into the inlet of the filter assembly using a syringe, the inlet of the filter assembly and the syringe typically have complementary configurations suitable for forming a seal between the one or more syringe and the filter assembly, as described herein with reference to the kit of the second aspect of the invention.

In embodiments in which the sample is introduced into the inlet of the filter assembly and passed through the filter assembly using a pump fixed to the inlet of the filter assembly, the inlet of the filter assembly and an outlet of the pump typically have complementary configurations suitable for forming a seal between the pump and the filter assembly. In embodiments in which the sample is introduced into the inlet of the filter assembly and passed through the filter assembly using a pump fixed to the outlet of the filter assembly, the outlet of the filter assembly and an inlet of the pump typically have complementary configurations suitable for forming a seal between the pump and the filter assembly. The complementary configurations of the inlet and/or outlet of the filter assembly and the outlet and/or inlet of the pump are typically as described herein with reference to the syringe and filter assembly of the kit of the second aspect of the invention.

In some embodiments, the method further comprises introducing a preservative into the filter assembly (e.g., subsequent to the filtered sample being passed out of the filter assembly), either via the inlet of the filter assembly or via the outlet. In such embodiments, the preservative is typically introduced into the filter assembly so as to contact eDNA retained within the filter assembly (e.g. on the first and/or second membrane). Preferably, the preservative is introduced into the filter assembly so as to substantially fill the entire interior of the filter assembly (e.g. 80% or more, preferably 85% or more, more preferably 90% or more, still more preferably 95% or more, still further preferably 99% or more of the entire interior of the filter assembly). In this context "the entire interior of the filter assembly" refers to volume within the filter assembly which is not occupied by internal components of the filter assembly (e.g. the first and second membranes) or material retained within the filter assembly after the sample has been passed through the filter assembly.

In some embodiments the preservative is effective to protect captured eDNA from degradation. Suitable preservatives which are effective to protect captured eDNA from degradation are known in the art and include ethanol, and products designed to stabilise biological samples and to protect RNA or DNA, such as RNAlater® (an aqueous, nontoxic tissue storage reagent that rapidly permeates tissues to stabilize and protect, cellular RNA, available from Sigma Aldrich) and DNAgard® (a liquid storage reagent that rapidly permeates cell membranes to stabilize and protect genomic DNA, available from Biomatrica).

In some embodiments the preservative is effective to protect captured eDNA from degradation and additionally effective to lyse material comprising eDNA and release DNA into solution. Suitable preservatives which are effective to protect captured eDNA from degradation and additionally effective to lyse material comprising eDNA and release DNA into solution include an aqueous solution comprising one or more of tris(hydroxymethyl)aminomethane (tris base), EDTA, NaCl, and sodium dodecyl sulfate (SDS).

Suitable preservatives are typically not toxic. Preferable preservatives are non-toxic and non-flammable.

In some embodiments, the method of the third embodiment of the invention further comprises a step of sealing the filter assembly (e.g. subsequent to introducing a preservative into the filter assembly). In such embodiments, the preservative is typically sealed inside the filter assembly. The step of sealing the filter assembly typically comprises sealing the inlet and/or the outlet of the filter assembly with one or more fluid impermeable cap. The one or more fluid impermeable cap is typically as described elsewhere herein in connection with the kit of the second embodiment of the invention.

In a fourth aspect, the present invention provides a method of providing eDNA comprising: providing a filter assembly comprising captured eDNA; and extracting eDNA from the filter assembly.

In some embodiments of the method of the fourth aspect of the invention, the provided filter assembly further comprises a preservative which is effective to protect captured eDNA from degradation, and the step of extracting eDNA comprises discarding the preservative, exposing material comprising the captured eDNA to a lysis buffer, and extracting eDNA from the lysis buffer.

In some embodiments of the method of the fourth aspect of the invention, the provided filter assembly further comprises a preservative which is effective to protect captured eDNA from degradation and additionally to lyse material comprising eDNA and release DNA into solution, and the step of extracting eDNA comprises removing the preservative comprising eDNA in solution from the filter assembly. In some such embodiments the step of extracting eDNA may further comprise the addition of a proteinase prior to removing the solution from the filter assembly. Addition of a proteinase in this way may aid lysis. Suitable proteinases include Proteinase K.

Certain non-limiting embodiments of the invention will now be described in more detail by reference to the drawings.

FIG. 1 shows a filter assembly 1 in accordance with an embodiment of the first aspect of the present invention, comprising a first membrane 3 a second membrane 4 a fluid-impermeable housing 2 having an inlet 5 and an outlet 6. The inlet 5 is disposed on a first face 2a of the fluid-impermeable housing 2, and the outlet 6 is disposed on a second face 2b of the fluid-impermeable housing 2. The inlet 5 and/or outlet 6 includes a valve 13 configured to allow fluid to pass through under pressure, but is sealed in the absence of pressure. The first membrane 3 is disposed within the fluid-impermeable housing 2 between the first face 2a of the fluid-impermeable housing 2 and the second face 2b of the fluid-impermeable housing 2, and the second membrane 4 is disposed within the fluid-impermeable housing 2 between the first membrane 3 and the second face 2b of the fluid-impermeable housing 2.

Figure 2:
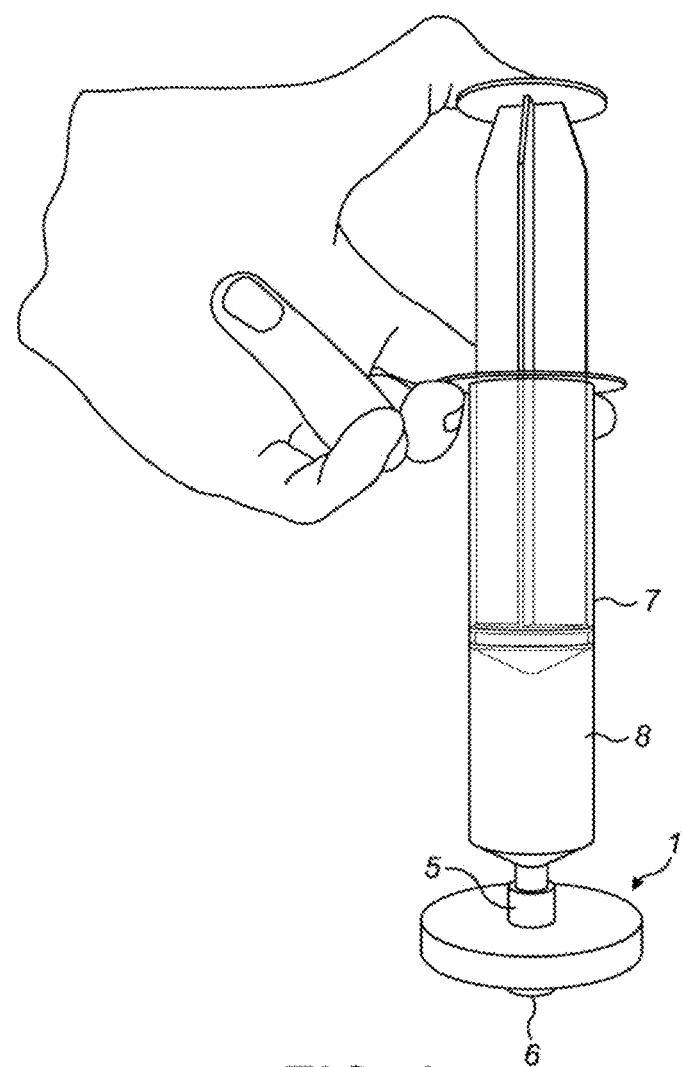
FIG. 2 shows introduction of a sample into a filter assembly in a step of an embodiment of the third aspect of the present invention.
Figure 3:
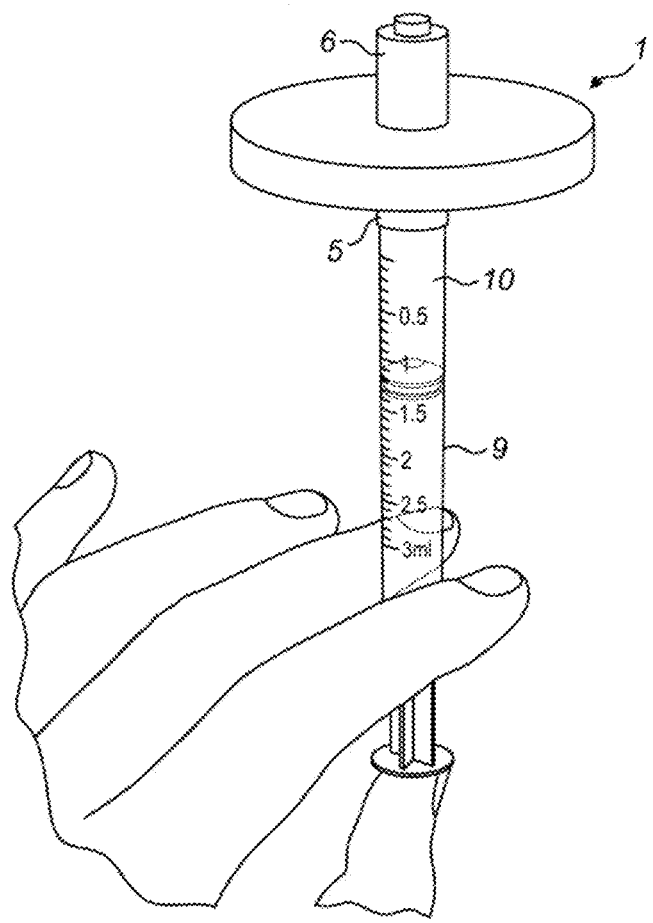
FIG. 3 shows introduction of a preservative into a filter assembly in a step of an embodiment of the third aspect of the present invention.
Figure 4:
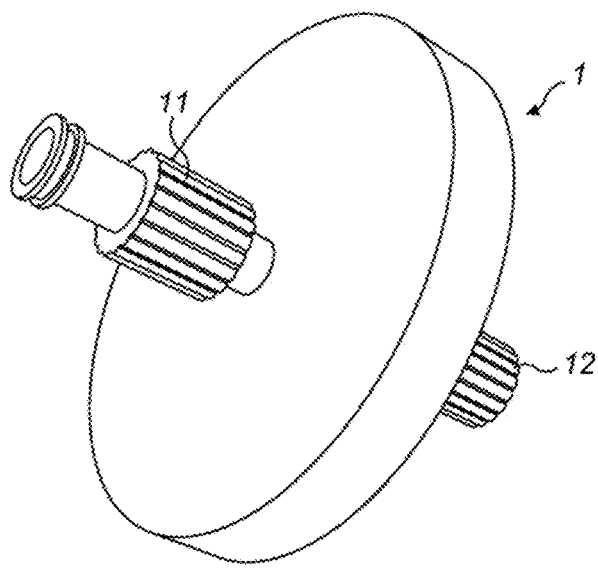
FIG. 4 shows a capped filter assembly in a step of an embodiment of the third aspect of the present invention.

FIGS. 2 to 4 show certain steps of an embodiment of the third aspect of the present invention in which a sample 8 is first introduced into an inlet 5 of a filter assembly 1 with a syringe 7. The sample 8 passes out of the outlet 6 of the filter assembly 1 (not shown) and the syringe 7 is removed from the inlet 6 (not shown). The filter assembly 1 is inverted so that the inlet 5 is below the outlet 6 and a second syringe 9 containing a preservative 10 is attached to the inlet 5. The preservative 10 is introduced from the second syringe 9 through the inlet 5 into the filter assembly 1 until the interior of the filter assembly 1 has been filled with preservative 10. Filing of the interior of the filter assembly 1 is confirmed when preservative 10 can be seen at the outlet 6 (not shown). With the outlet 6 still above the inlet 5, the outlet 6 is capped with a fluid-impermeable cap 12. The filter assembly 1 is then re-inverted so that the inlet 5 is above the outlet 6, the second syringe 9 is removed from the inlet 5 (not shown) and the inlet 5 is capped with a fluid impermeable cap 11.

EXAMPLES

Example 1

A filter assembly as illustrated in FIG. 1 is provided having a first glass fibre (GF) membrane with a pore size of 5 μm and a second polyethersulfone (PES) membrane with a pore size of 0.8 μm. A sample is taken from a pond and filtered through the filter assembly, introducing the sample into the inlet of the filter assembly using a syringe and passing the filtered sample out of the filter assembly through the outlet. A preservative solution comprising SDS, EDTA and sodium chloride is introduced into the filter assembly in an upwards direction through the inlet using a second syringe until the preservative appears at the outlet of the filter assembly. The inlet and the outlet of the filter assembly are capped and the filled filter assembly is transported for analysis of the captured eDNA.

Comparative Example 1

A sample from the same source as that used in Example 1 is passed through an exposed PES membrane with a pore size of 0.8 μm. The membrane is transported for analysis of the captured eDNA.

The membrane of Comparative Example 1 permits less of the sample to be filtered than the filter assembly of Example 1 before becoming clogged with particulate matter present in the sample. Analysis of Comparative Example 1 detects less eDNA than for Example 1. Comparative Example 1 shows signs of contamination during transport, whereas Example 1 does not.

Example 2

Samples have been filtered using a range of different filters to compare the performance in terms of the average volume of sample it is possible to filter, and the average DNA concentration detected following filtration. The results are set out in the table below:

| | Average volume (ml) | Standard deviation | Average DNA Concentration (ng/ml) |
|---|---|---|---|
| Filter 1 | 27.13 | 6.47 | 0.22 |
| Filter 2 | 50.83 | 10.21 | 0.45 |
| Filter 3 | 61.43 | 7.48 | 0.24 |
| Filter 4 (industry standard) | 178 | 25.88 | 0.90 |
| 0.8 μm pore filter | 268.33 | 60.14 | 1.57 |
| 1.2 μm pore filter | 338.33 | 65.55 | 3.55 |
| 0.8 μm filter + prefilter | 965 | 191.22 | 9.08 |

Filter 1 was a cellulose membrane (Alpha cellulose) with a pore size of 0.45 μm. The volume of sample filtered varied between 22 and 26 ml, with the concentration of DNA captured ranging from 0.112 to 0.34 ng/ml over 4 repetitions.

Filter 2 was a PES membrane with a pore size of 0.22 μm (from Fischer Scientific). The volume of sample filtered varied between 50 and 70 ml, with the concentration of DNA captured ranging from 0.212 to 0.776 ng/ml over 3 repetitions.

Filter 3 was a PVDF membrane with a pore size of 0.45 μm (from Fischer Scientific). The volume of sample filtered varied between 50 and 70 ml, with the concentration of DNA captured ranging from 0.0708 to 0.382 ng/ml over 3 repetitions.

Filter 4 is the industry standard filter for filtering environmental samples for the capture of eDNA. It was a PVDF membrane with a pore size of 0.45 μm (from Sterivex). The volume of sample filtered varied between 160 and 210 ml, with the concentration of DNA captured ranging from 0.297 to 1.7 ng/ml over 4 repetitions.

The 0.8 μm pore filter was a PES membrane with a pore size of 0.8 μm (from Sterlitech). This is not a filter membrane conventionally used for this purpose. The volume of sample filtered varied between 180 and 350 ml, with the concentration of DNA captured ranging from 0.912 to 3.06 ng/ml over 4 repetitions.

The 1.2 μm pore filter was a PES membrane with a pore size of 1.2 μm (from Sterlitech). This is not a filter membrane conventionally used for this purpose. The volume of sample filtered varied between 220 and 420 ml, with the concentration of DNA captured ranging from 1.32 to 5.56 ng/ml over 4 repetitions.

The combination of the 0.8 µm PES membrane (from Sterlitech) with a glass fibre prefilter having a pore size of 5 µm is in accordance with the invention. The volume of sample filtered varied between 800 and 1210 ml, with the concentration of DNA captured ranging from 2.22 to 16 ng/ml over 4 repetitions.

It is clear from the data what a striking difference the use of the filter assembly of the invention makes to the efficiency of the assembly at capturing eDNA. The two-membrane arrangement minimises clogging of the pores as the sample is passed through the filter assembly. The filter assembly also captures more eDNA per ml of the sample, which in turn means that a greater amount of eDNA is available for analysis. This means that the use of the filter assemblies, kits and methods of the present invention allows for much more accurate testing of the samples collected.

Certain features of the aspects of the present invention are described herein with reference to certain embodiments. It will be evident that the present disclosure extends to combinations of those embodiments.

Aspects of the present invention have been described herein with reference to certain embodiments. However, the invention is not limited thereto. Rather the invention should be understood as being defined by the scope of the appended claims, with due account being taken of any equivalents thereto.

What is claimed is:

1. A filter assembly comprising: a first membrane; a second membrane; a fluid-impermeable housing; an inlet; and an outlet, wherein the inlet is configured to form a fluid-impermeable seal with an outlet of a syringe and/or a pump, wherein the inlet and/or outlet comprises a valve configured to allow fluid to pass through under pressure, but is sealed in the absence of pressure.

2. The filter assembly according to claim 1, wherein the inlet is disposed on a first face of the fluid-impermeable housing, and the outlet is disposed on a second face of the fluid-impermeable housing.

3. The filter assembly according to claim 2 wherein the first membrane is disposed within the fluid-impermeable housing between the first face of the fluid-impermeable housing and the second face of the fluid-impermeable housing, and the second membrane is disposed within the fluid-impermeable housing between the first membrane and second face of the fluid-impermeable housing.

4. The filter assembly according to claim 1, wherein the first membrane and/or the second membrane are fluid permeable.

5. The filter assembly according to claim 1, wherein the first membrane has a first pore size of 1 µm or more, and the second membrane has a second pore size of 1 µm or less.

6. The filter assembly according to claim 5, wherein the first pore size is from 4 µm to 6 µm.

7. The filter assembly according to claim 5, wherein the second pore size is from 0.7 µm to 0.9 µm.

8. The filter assembly according to claim 1, wherein the inlet and/or the outlet is configured to form a fluid-impermeable seal with a fluid-impermeable cap.

* * * * *